(12) United States Patent
Susko-Parrish et al.

(10) Patent No.: US 6,680,199 B1
(45) Date of Patent: *Jan. 20, 2004

(54) IN VITRO ACTIVATION OF MAMMALIAN OOCYTES

(75) Inventors: Joan L. Susko-Parrish, Monona, WI (US); David L. Northey, Madison, WI (US); M. Lorraine Leibfried-Rutledge, Madison, WI (US); Steven L. Stice, DeForest, WI (US)

(73) Assignee: Infigen, Inc., Deforest, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/576,592

(22) Filed: May 22, 2000

Related U.S. Application Data

(60) Continuation-in-part of application No. 09/176,395, filed on Oct. 21, 1998, now Pat. No. 6,077,710, which is a continuation of application No. 08/610,744, filed on Mar. 4, 1996, now Pat. No. 6,194,202, which is a division of application No. 08/016,703, filed on Feb. 10, 1993, now Pat. No. 5,496,720.

(51) Int. Cl.$^7$ .............................. C12N 5/00; C12N 5/02
(52) U.S. Cl. ....................................... 435/375; 435/325
(58) Field of Search ................................ 435/375, 325; 800/24

(56) References Cited

U.S. PATENT DOCUMENTS

| | | | |
|---|---|---|---|
| 4,994,384 A | 2/1991 | Prather et al. | 800/24 |
| 5,096,822 A | 3/1992 | Rosenkrans | 435/388 |
| 6,077,710 A | * 6/2000 | Susko-Parrish et al. | 435/375 |

OTHER PUBLICATIONS

Collas, P. and J.M. Robl. 1990. "Factors affecting the efficiency of nuclear transplantation in the rabbit embryo." Biol. Reprod. 43:877–884.

Cuthbertson, K.S.R. 1983. "Parthenogenic activation of mouse oocytes in vitro with ethanol and benzyl alcohol." J. Exp. Zool. 226:311–314.

First, N. L., Leibfried–Rutledge, M.L., Northey, D.L. and Nuttleman, P.R. 1992. "Use of in vitro matured oocytes 24 h of age in bovine nuclear transfer." Theriogenology 37:211.

First, N. L. and R. Prather. 1991. "Genomic Potential in Mammals," Differentiation, 48:1–8.

Fissore, R.A. and J.M. Robl. 1992. "Intracellular Ca2+ response of rabbit oocytes to electrical stimulation." Mol. Reprod. Dev. 32:9–16.

Graham, C.F. 1969. "The fusion of cells with one and two cell mouse embryos," Wistar Inot. Symp. Monogr., 9:19.

Graham, C.F. 1970. "Parthenogenic mouse blastocysts." Nature 242:475–476.

Graham, C.F. 1974. "The production of parthenogenetic mammalian embryos and their use in biological research." Biol. Rev. 49:399–422.

Gray, K.R., K.R. Bondiolo and C.L. Betts. 1991. "The commercial application of embryo splitting in beef cattle." Theriogenology 35:37–45.

Kaufman, M. H. 1981. Parthenogenesis: a system facilitating understanding of factors that influence early mammalian development. Prog. in Anat., vol. 1, 1–34.

Kline, D. and Kline, J.T. 1992. "Repetitive calcium transients and the role of calcium in exocytosis and cell cycle activation in the mouse egg." Dev. Biol. 149:80–89.

Kubiak, J. 1989. "Mouse Oocytes Gradually Develop the Capacity for Activation during the Metaphase II Arrest." Dev. Biol. 136:537–545.

Masui, Y. and Markert, C. L. 1971. "Cytoplasmic control of nuclear behavior during meiotic maturation of frog oocytes." J. Exp. Zool. 177, 129–146.

McGrath, J. and Solter, D. 1983. "Nuclear Transplantation in the Mouse Embryo by Microsurgery and Cell Fusion." Science, vol. 220, 1301–1302.

Nagai, T. 1987. "Parthenogenic activation of cattle follicular oocytes in vitro with ethanol." Gamete Res. 16:243–249.

Nurse, P. 1990. "Universal control mechanism regulating onset of M–phase." Nature 344:503–508.

Onodera, M. and Y. Tsunoda. 1989. "Parthenogenetic activation of mouse and rabbit eggs by electric stimulation in vitro." Gamete Research 22:277–283.

Ozil, J.P. 1990. "The parthenogenetic development of rabbit oocytes after repetitive pulsatile electrical stimulation." Development 109:117–127.

Rickords, L.F. and White, K.L. 1992. "Electrofusion–induced intracellular Ca+2 flux and its effect on murine oocyte activation." Mol. Reprod. Dev. 31:152–159.

Siracusa, G., Whittingham, D.G., Molinaro, M. and Vivarelli, E. 1978. "Parthenogenic activation of mouse oocytes induced by inhibitors of protein synthesis." J. Embryol. exp. Morph. 43:157–166.

Sirard, M.A., J.J. Parrish, C.B. Ware, M.L. Leibfried–Rutledge and N.L. First. 1988. "The culture of bovine oocytes to obtain developmentally competent embryos." Biol. Reprod. 39:546–552.

Steinhardt, R.A., Epel, D. and Yanagimachi, R. 1974. "Is calcium ionophore a universal activator for unfertilized eggs?" Nature 252:41–43.

Stice, S.L. and Robl, J.M. 1990. "Activation of mammalian oocytes by a factor obtained from rabbit sperm." Mol. Reprod. Dev. 25:272–280.

(List continued on next page.)

*Primary Examiner*—Anne-Marie Falk
(74) *Attorney, Agent, or Firm*—Foley & Lardner

(57) ABSTRACT

A process of parthenogenic activation of mammalian oocytes which includes increasing intercellular levels of divalent cations in the oocyte; and reducing phosphorylation of cellular proteins in the oocyte. One method of accomplishing this is by introducing $Ca^{2+}$free cation, such as ionomycin, to the oocyte and then preventing phosphorylation of the cellular proteins within the oocyte by adding a serine-threonine kinase inhibitor, such as 6-dimethylaminopurine (DMAP).

22 Claims, 4 Drawing Sheets

OTHER PUBLICATIONS

Stice, S.L. and Keefer, C. 1992. "Improved developmental rates for bovine nucleus transfer embryos using cold shock activated oocytes." Biol. Reprod. 42 (Suppl 1):166.

Surani, M.A.H. and Kaufmann, N.H. 1977. "Influence of extracellular Ca2+ and Mg2+ ions on the second meiotic division of mouse oocytes: Relevance to obtaining haploid and diploid parthenogenetic embryos." Dev. Biol. 59:86–90.

Swann, K. 1990. "A cytosolic sperm factor stimulates repetitive calcium increases and mimics fertilization in hamster eggs." Development 110:1295–1302.

Tarkowski, A.K., Witkowska, A. and Nowicka, J. 1970. "Experimental parthenogenesis in the mouse." Nature 226:162–165.

Tarkowski, A.K. 1975. "Recent studies on parthenogenesis in the mouse." In: The Developmental Biology of Reproduction (C.L. Markert, E.J. Papaconstantinon, eds.), pp. 107–129, New York: Academic Press.

Ware, C.B., Barnes, F.L., Maiki–Laurila, M. and First, N.L. 1989. "Age dependence of bovine oocyte activation." Gamete Res. 22:265–275.

Whitaker, M. and Irvine, F.R. 1984. "Inositol 1,4,5–trisphophate microinjection activates sea urchin eggs." Nature (London) 312:636–639.

Yang, X., Jiang, S. and Shi, Z. 1992. "Improved activation by combined cycloheximide and electride pulse treatment of bovine follicular oocytes matured in vitro for 23–24 hours." Biol. Reprod. 42(Suppl 1): 117.

Yang, X. et al., 1990, "Potential of hypertonic medium treatment for embryo micromanipulation: II: Assessment of nuclear transplantation methodology, isolation, subzona insertion and electrofusion of blastomeres," Mol. Reprod. Dev. 27:118–129.

Yang, X. et al., 1991, "Nuclear transfer in rabbits and cattle by electric pulse–induced fusion of blastomeres to enucleated oocytes," Theriogenology 35:298 (abs).

* cited by examiner

IN VITRO ACTIVATION OF MAMMALIAN OOCYTES

This application is a continuation in part of U.S. application Ser. No. 09/176,395, filed on Oct. 21, 1998 and issued on Jun. 20, 2002 as U.S. Pat. No. 6,077,710, which is a continuation of U.S. application Ser. No. 08/610,744, filed on Mar. 4, 1996 and issued on Feb. 27, 2001 as U.S. Pat. No. 6,194,202, which is a divisional of U.S. patent application Ser. No. 08/016,703, filed on Feb. 10, 1993 and issued on Mar. 5, 1996 as U.S. Pat. No. 5,496,720, each of which is hereby incorporated by reference in its entirety.

FIELD OF THE INVENTION

The present invention is generally directed to an improved process for cloning or multiplying mammalian embryonic cells and to an improved process for transferring the nuclei of donor embryonic cells into enucleated recipient oocytes. The present invention is specifically directed to a process for parthenogenically activating mammalian oocytes and to the use of the oocytes.

CITATION OF REFERENCES

A full citation of the references appearing in this disclosure can be found in the section preceding the Claims.

DESCRIPTION OF THE PRIOR ART

Advanced genetic improvement and selection techniques continue to be sought in the field of animal husbandry. With specific reference to dairy cattle, for example, significant increases in milk production have been made with the wide scale use of genetically superior sires and artificial insemination. Dairy cows today produce nearly twice as much milk as they did 30 years ago. Further genetic improvement can be accomplished by the multiplication of superior or genetically manipulated animals by cloning using embryonic cells. For purposes of the present invention, the term "embryonic cell" refers to embryos and cells cultured from embryos including embryonic stem cells.

It has now become an accepted practice to transplant embryonic cells in cattle to aid in the production of genetically superior stock. The cloning of embryonic cells together with the ability to transplant the cloned embryonic cells makes it possible to produce multiple genetically identical animals. Embryonic cell cloning is the process of transferring the nucleus of an embryonic donor cell to an enucleated recipient ovum or oocyte. The clone then develops into a genetically identical offspring to the donor embryonic cell.

Nuclear Transfer

The ability to produce multiple copies of genetically identical individuals from embryonic cells derived from a single embryo provides a means for embryonic cell selection where the cloned lines descending from one embryo could be selected by progeny testing for further clonal multiplication. Nuclear transfer creates the possibility of permitting rapid changes in animal characteristics such as meat and milk production. Nuclear transfer is one process for producing multiple copies of an embryo. Reference is made to *First and Prather* (1991) and U.S. Pat. No. 4,994,384 to *Prather et al.*, which are incorporated herein by reference, for a description of nuclear transfer.

Briefly, nuclear transfer involves the transfer of an embryonic cell or nucleus from an embryonic cell. Either entity is derived from a multicellular embryo (usually 20 to 64-cell stage) into an enucleated oocyte, an oocyte with the nucleus removed or destroyed. The oocyte then develops into a multi-cellular stage and is used to produce an offspring or as a donor in serial recloning.

Cloning by nuclear transfer has great potential for the multiplication of genotypes of superior economic value (*Gray et al.*, 1991). Nuclear transfer to produce identical offspring has many advantages over embryo splitting or embryonic cell aggregation to produce fetal placental chimeras: 1) multiple copies of superior, genetically identical animals are possible; 2) embryonic cell sexing and cryopreservation may be applied to the cloning scheme allowing all clones to be of preselected sex; and 3) embryonic cells from different genetic strains can be frozen and can be multiplied after testing.

Oocyte Activation

Cattle ovulate spontaneously approximately every 21 days, about 24–36 hours after a surge of luteinizing hormone (LH). In vivo and in vitro matured oocytes are activated by entry of sperm into the oocyte. Activation by sperm can occur in bovine oocytes matured in vitro as early as 15 hours. However, currently oocytes must be matured for more than about 28 hours to respond to parthenogenic activation stimuli. This datum implies that either the sperm provide a factor necessary for oocyte activation (*Whitaker and Irvine*, 1984; *Stice and Robl*, 1990; *Swann*, 1990) or that processes that increase intracellular calcium alone are not sufficient in the bovine oocyte to overcome the cytostatic factor(s).

The stage of maturation of the oocyte at enucleation and nuclear transfer is important (*First and Prather*, 1991). In general, successful mammalian embryonic cell cloning practices use the metaphase II stage oocyte as the recipient oocyte. At this stage, it is believed the oocyte is sufficiently "activatable" to treat the introduced nucleus as it does a fertilizing sperm.

Activation of mammalian oocytes involves exit from meiosis and reentry into the mitotic cell cycle by the secondary oocyte and the formation and migration of pronuclei within the cell. Viable oocytes prepared for maturation and subsequent activation are required for nuclear transfer techniques.

Activation requires cell cycle transitions. The maturation Promoting Factor complex becomes essential in the understanding of oocyte senescence and age dependent responsiveness to activation. MPF activity is partly a function of calcium ($Ca^{2+}$). A major imbalance in the components of the multi-molecular complex which is required for cell cycle arrest may be responsible for the increasing sensitivity of oocytes to activation stimuli during aging.

Parthenogenetic Activation

Parthenogenic activation of oocytes may be used instead of fertilization by sperm to prepare the oocytes for nuclear transfer. Parthenogenesis is the "production" of embryonic cells, with or without eventual development into an adult, from a female gamete in the absence of any contribution from a male gamete (*Kaufman* 1981).

Parthenogenetic activation of mammalian oocytes has been induced in a number of ways. Using an electrical stimulus to induce activation is of particular interest because electrofusion is part of the current nuclear transfer procedure. *Tarkowski, et al.*(1970) reported successful use of electric shock to activate the mouse ova while in the oviduct. Parthenogenetic activation in vitro by electrical stimulation with electrofusion apparatus used for embryonic cell-oocyte membrane fusion has been reported (*Stice and Robl*, 1990; *Collas and Robl*, 1990); *Onodera and Tsunoda*, 1989). In the rabbit, with the combined AC and DC pulse 80 to 90 percent of freshly ovulated oocytes have been activated (*Yang, et al.*, (1990, 1991). *Ozil* (1990) used multiple electrical pulses to induce adequate activation of rabbit oocytes. Adapting this for nuclear transfer, *Collas and Robl* (1990) obtained improved development to term.

It is believed that the most effective activating stimulus would be one that mimicked the response of mammalian oocytes to fertilization. One such response of rabbit oocytes is characterized by repetitive transient elevations in intracellular $Ca^{2+}$ levels followed by rapid return to base line (*Fissore and Robl*, 1992), which may explain the improved development with activation by multiple electrical pulses.

Parthenogenic activation of metaphase II bovine oocytes has proven to be more difficult than mouse oocytes. Mouse oocytes have been activated by exposure to $Ca^{+2}$-$Mg^{+2}$ free medium (*Surani and Kaufman*, 1977), medium containing hyaluronidase (*Graham*, 1970), exposure to ethanol (*Cuthbertson*, 1983), $Ca^{+2}$ ionophores or chelators (*Steinhardt et al.*, 1974; *Kline and Kline*, 1992), inhibitors of protein synthesis (*Siracusa et al.*, 1978) and electrical stimulation (*Tarkowski et al.*, 1970). These procedures that lead to high rates of parthenogenic activation and development of mouse oocytes do not activate young bovine oocytes and/or lead to a much lower development rate. Fertilization and parthenogenic activation of mouse oocytes is also dependent on post ovulatory aging (*Siracusa et al.*, 1978).

Activation of bovine oocytes has been reported by ethanol (*Nagai*, 1987), electrical stimulation (*Ware et al.*, 1989), exposure to room temperature (*Stice and Keefer*, 1992), and a combination of electrical stimulation and cycloheximide (*First et al.*, 1992; *Yang et al.*, 1992). While these processes are thought to raise intracellular $Ca^{+2}$ (*Rickord and White*, 1992), they are most successful when the oocytes have been aged for more than 28 hours of maturation (*Ware et al.*, 1989).

SUMMARY OF THE INVENTION

The present invention is directed to a process for parthenogenically activating mammalian oocytes comprising increasing intercellular levels of divalent cations in the oocyte and reducing phosphorylation of cellular proteins in the oocyte. Reducing phosphorylation can be achieved by inhibiting phosphorylation or preventing phosphorylation according to procedures explained in this disclosure. The present invention is also directed to a parthenogenically-activated oocyte produced by this process.

The present invention is further directed to a process for parthenogenically activating a 10–52 hour mammalian oocyte comprising increasing intercellular levels of divalent cations in the oocyte by introducing a divalent cation into the oocyte cytoplasm, and reducing phosphorylation of cellular proteins in the oocyte wherein phosphorylation of cellular proteins is reduced by adding an effective phosphorylation inhibiting amount of a serine-threonine kinase inhibitor to the oocyte.

The present invention is also directed to a method for transferring a nucleus from a donor embryonic cell to a parthenogenically-activated recipient oocyte and culturing the resulting nuclear transferred embryo in vitro or in vivo comprising collecting the embryonic cell; isolating a membrane-bound nucleus from the embryonic cell; collecting recipient oocytes from donor animals or their products in vitro; parthenogenically activating the recipient oocytes, wherein the oocytes are activated by a process comprising increasing intercellular levels of divalent cations in the oocyte and reducing phosphorylation of cellular proteins in the oocyte; transferring the nucleus to the enucleated recipient parthenogenically-activated oocyte to form a nuclear transferred oocyte; and forming a single cell embryo from the nuclear transferred oocyte.

The present invention allows nuclear transfer processes to proceed with younger oocytes such as a 24-hour oocyte, which may produce healthier embryonic cells. There is evidence indicating that early oocyte activation allows for better development of the nuclear transplanted cell. The 24-hour oocyte is the approximate age of an in vivo oocyte during natural fertilization.

Another advantage to activating younger oocytes is the ability, in the laboratory, to obtain a faster turn around time. Within the procedure of the current art, a typical oocyte is a 41–43 hour oocyte. Therefore, the oocyte used in nuclear transfer technology is typically 17–19 hours older than an oocyte used within the process of the present invention which, for example, allows a 24-hour oocyte to be activated.

The younger oocyte potentially allows for tests to be performed in a shorter time period. Further, the laboratory is operated more efficiently with faster turn around of test results. In industry, the use of a younger oocyte will allow progeny to be produced in less time.

Further objects, features and advantages of the present invention will be apparent from the following detailed description when taken in conjunction with the accompanying drawings.

DETAILED DESCRIPTION OF THE INVENTION

Figure 1A:
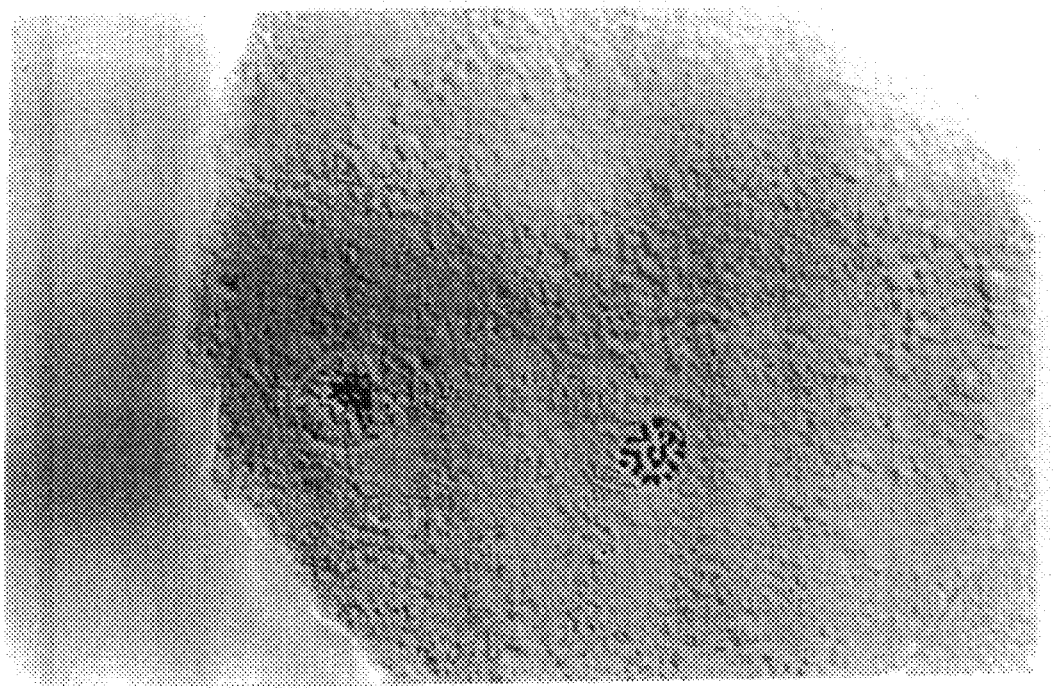
FIG. 1*a* is a photograph illustrating a metaphase II bovine oocyte from the control treatment in Experiment 1.

The overall procedure disclosed herein may be described as cloning or as multiplication of embryonic cells from an embryo by nuclear transfer followed by a prolonged maintenance period to increase fusion and developmental rates of multiple genetically identical embryonic cells, and ultimately, animals.

In vitro matured bovine oocytes require both an increase in $Ca^{2+}$ and a reduction in phosphorylation to cause activation and subsequent entry into the cell cycle. Increases in $Ca^{2+}$ cation alone are sufficient to cause resumption of mitosis and extrusion of the second polar body, but not pronuclear formation. Additional treatment to reduce phosphorylation in cellular proteins suppresses second polar body extrusion and allows the oocyte to continue as if in mitosis. The oocytes then resume cell cycles and can initiate limited early pregnancy responses in utero.

Although it is contemplated that the procedure of the present invention may be utilized on a variety of mammals, the procedure will be described with reference to the bovine species. However, the present invention does not restrict the cloning procedure to bovine embryonic cells.

Oocyte

The term "oocyte," as used here for the recipient oocyte, means an oocyte which develops from an oogonium and, following meiosis, becomes a mature ovum. It has been found that not all oocytes are equally optimal cells for efficient nuclear transplantation in mammals. For purposes of the present invention, metaphase II stage oocytes, matured either in vivo or in vitro, have been found to be optimal. Mature metaphase II oocytes may be collected surgically from either nonsuperovulated or superovulated cows or heifers 24–48 hours past the onset of estrus or past an injection of human Chorionic Gonadotrophin (hcG) or similar hormone. Alternatively, immature oocytes may be recovered by aspiration from ovarian follicles obtained from slaughtered cows or heifers and then may be matured in vitro in a maturation medium by appropriate hormonal treatment and culturing. As stated above, the oocyte is allowed to mature in a known maturation medium until the oocyte enters the metaphase II stage, generally 16–24 hours post aspiration. For purposes of the present invention, this period of time is known as the "maturation period." As used herein for calculation of time periods, "aspiration" refers to aspiration of the immature oocytes from ovarian follicles.

Maintenance Media

There are a variety of oocyte culture and maintenance media routinely used for the collection and maintenance of oocytes, and specifically bovine oocytes. Examples of known media, which may be used for bovine oocyte culture and maintenance, include Ham's F-10+10% fetal calf serum, Tissue Culture Medium-199 (TCM-199)+10% fetal calf serum, Tyrodes's-Albumin-Lactate-Pyruvate (TALP), Dulbecco's Phosphate Buffered Saline (PBS), Eagle's and Whitten's media. One of the most common media used for the collection and freezing of embryonic cells is TCM-199 and 1 to 20% serum supplement including fetal calf serum, new born serum or steer serum. A preferred maintenance medium includes TCM-199 with Earle's salts, 10% fetal calf serum, 0.2 mM Na-pyruvate and 25 ug/ml gentamicin sulphate.

Another maintenance medium is described in U.S. Pat. No. 5,096,822 to *Rosenkrans et al.*, which is incorporated herein by reference. This medium, named CR1, contains the nutritional substances necessary to support an oocyte.

CR1 contains hemicalcium L-lactate in amounts ranging from 1.0 mM to 10 mM, preferably 1.0 mM to 5.0 mM. Hemicalcium L-lactate is L-lactate with a hemicalcium salt incorporated thereon. Hemicalcium L-lactate is significant in that a single component satisfies two major requirements in the culture medium: 1) the calcium requirement necessary for compaction and cytoskeleton arrangement; and 2) the lactate requirement necessary for metabolism and electron transport. Hemicalcium L-lactate also serves as valuable mineral and energy source for the medium necessary for viability of the oocytes.

Examples of the main components in CR1 medium include hemicalcium L-lactate, sodium chloride, potassium chloride, sodium bicarbonate and a minor amount of fatty-acid free bovine serum albumin. Additionally, a defined quantity of essential and non-essential amino acids may be added to the medium. CR1 with amino acids is known by the abbreviation "CR 1aa."

CR1 medium preferably contains the following components in the following quantities:

| | |
|---|---|
| sodium chloride - | 114.7 mM |
| potassium chloride - | 3.1 mM |
| sodium bicarbonate - | 26.2 mM |
| hemicalcium L-lactate - | 5 mM |
| fatty-acid free BSA - | 3 mg/ml |

Stripping the Oocytes

Prior to activation, the cumulus cells are stripped from the oocytes. Cumulus cells are non-reproductive or somatic cells which surround the oocyte and are believed to provide both protection and nutrients needed to mature the oocyte. The presence of cumulus cells creates a cloud around the oocytes making it very difficult if not impossible to observe oocytes during the maturation period.

Cumulus cells are stripped from an oocyte mechanically by pipetting cumulus enclosed oocytes (CEOs) through the neck of the micropipette (180–210 µm inner diameter) attached to a syringe. Cumulus cells fall off and denuded oocytes are removed from the maintenance medium. Cumulus cells are further disaggregated mechanically by pipetting them through the neck of the micropipette (20–30 µm inner diameter).

Other methods of stripping cumulus cells from an oocyte include removing the cells by vortexing approximately 200 µl of the TALP medium with the oocyte for approximately 3 minutes. Alternatively, the cells may be mechanically stripped by ultrasound techniques known to the art. The cells may also be stripped enzymatically by the application of proper enzymes such as trypsin or collagenase according to methods known to the art of cell culture.

Washing the Oocytes

The oocytes are then washed according to methods known to the art and moved to a maintenance medium, examples of which are described above. The time the oocytes are placed in the maintenance medium is designated "0 hour." Thus, for purposes of this disclosure, the age of the oocyte is the timed from the placement of the oocyte in the medium. A "24-hour oocyte" is therefore an oocyte which has been in the medium for 24 hours.

The oocytes are allowed to mature in the medium for approximately 10–50 hours, preferably about 20–26 hours, and most preferably about 24 hours under maintenance conditions, e.g., 39° C. with 5% $CO_2$ in air and maximal humidity.

Calcium Introduction

The oocyte is then introduced into a medium that causes the introduction of free calcium ion into the oocyte cytoplasm. Intracellular calcium concentration can be increased by any of the processes known in the art such as use of an ionophore such as ionomycin or A23187, by electric shock, ethanol treatment, caged chelators which can release calcium inside the cell in response to specific wavelengths, thapsegardin or depolarizing oocyte membrane (KCl or $NH_4Cl$). Magnesium or other divalent cations such as strontium and barium may also be introduced to the medium and oocyte in lieu of $Ca^{2+}$. Calcium is located in the cell membrane, mitochondria, endoplasmic reticula and other parts of the cell as well as externally to the oocyte before being released by the known processes and introduced as free $Ca^{2+}$ion into the oocyte cytoplasm.

Without wishing to be restricted to one source of explanation, it appears that the initial calcium transient appears to be an upstream event which activates a cascade of cellular changes necessary for resumption of meiosis and the cell cycle.

Reducing Phosphorylation in Cellular Proteins

The second phase of the invention contemplates the reduction of phosphorylation in cellular proteins. Cellular proteins are loosely defined as the proteins within a cell. A non-limiting list of examples include Maturation Promoting Factor (MPF), Cytostatic Factor (CSF), cytoskeletal proteins such as tubulin, and cyclins. There are essentially two ways to reduce phosphorylation in cellular proteins: (1) inhibiting phosphorylation, and (2) dephosphorylation.

Inhibition of phosphorylation is related to changes in cell cycle regulators such as MPF and CSF. MPF controls the release of oocytes from the prophase block, which promotes nuclear envelope disruption, chromosome condensation, and spindle formation (*Masui & Markert*, 1971). MPF is a complex of cdc2 and cyclin B whose activity is regulated by specific phosphorylation and dephosphorylation (*Nurse*, 1990). CSF arrests the cell cycle in metaphase, achieved through MPF activity. The c-mos protein, a component of CSF, may activate or stabilize MPF by regulating the stability of cyclin B stability.

Only the initial $Ca^{2+}$ surge induced by ionophore, electric shock or other methods is required since $Ca^{2+}$ induced transient will continue in the absence of the initial stimulus. The oocyte is then introduced to a chemical mechanism that prevents phosphorylation of serine and threonine amino acids in other proteins within the oocyte allowing a cascade of events to occur. The cascade includes cortical and zona pellucida reactions associated with activation.

The chemical mechanism may include a serine-threonine kinase inhibitor such as 6-dimethylaminopurine (DMAP), staurosporine, 2-aminopurine, and sphingosine to prevent phosphorylation of serine and threonine which induces the cascade.

The serine-threonine kinase inhibitor is thought to inhibit MPF and CSF activity by inhibiting the specific protein kinases that activate and deactivate these complexes. Inhibition of phosphorylation allows the oocyte to escape from metaphase II and continue as if in mitosis, thereby parthenogenically activating the oocyte.

The serine-threonine kinase inhibitor may also be important in inhibiting phosphorylations necessary for the spindle apparatus (by inhibiting c-mos) thus inhibiting expulsion of the second polar body. Further elucidation of the molecular events of activation are necessary. The need for an initial calcium transient appears to be universal but the pathways which regulate the subsequent cascade of events leading to parthenogenic development may be different in bovine oocytes than any others thus far studied.

The mechanism may also include a phosphatase which dephosphorylizes the 2 amino acids, thus, preventing a further cascade. Phosphatase 2A and phosphatase 2B have been implicated in the second messenger systems important in oocyte activation.

Nuclear Transfer

Parthenogenically-activated oocytes can be used in nuclear transfer processes. Reference is made to U.S. Pat. No. 4,994,384 to Prather et al. (*Prather et al.*), which is incorporated herein by reference for a general discussion on nuclear transfer techniques.

Culture of Recipient Oocytes

For the successful commercial use of techniques such as genetic engineering, nuclear transfer or cloning, the process generally requires collecting immature (prophase I) oocytes from mammalian ovaries obtained at a slaughterhouse and maturing the oocytes in a maturation medium prior to activation until the oocytes enters the metaphase II stage, generally 18–24 hours post-aspiration. For purposes of the present invention, this period of time is known as the "maturation period." As used herein for calculation of time periods, "aspiration" refers to aspiration of the immature oocyte from ovarian follicles.

The stage of maturation of the oocyte at enucleation and nuclear transfer is important (*First and Prater*, 1991). In general, successful mammalian embryo cloning practices use the metaphase II stage oocyte as the recipient oocyte. At this stage, it is believed the oocyte is sufficiently "activatable" to treat the introduced nucleus as it does a fertilizing sperm. In domestic animals, and especially cattle, the oocyte activation period is between about 16–52 hours, preferably about 28–42 hours, and most preferably about 24 hours post-aspiration.

Approximately 16–24 hours after the initiation of oocyte maturation, the oocytes are stripped of cumulus cells according to the processes. The cumulus cells are a mass of somatic cells which surround the oocyte in vivo. The cumulus cells provide both protection and the nutrients needed to mature the oocyte.

Activation

The oocytes are then parthenogenically activated according to the processes discussed previously. For example, the oocytes can be exposed to an appropriate quantity, e.g., 5 $\mu$M, ionomycin in TL-HEPES for approximately 4 minutes. The oocytes can then be diluted in TL-HEPES with bovine serum albumin [BSA]. The oocytes can then be placed into an appropriate activation medium, e.g., CR1, containing DMAP for approximately 3.5–5 hours. Following incubation in DMAP, the oocytes are diluted in TL-Hepes (1 mg/ml BSA) and incubated in CR1aa.

Micromanipulation of Oocytes

Micromanipulation of the oocytes is performed in a manner similar to the methods of *McGrath and Solter*, 1983, which is incorporated herein for details of the micromanipulation technique. Manipulation is performed in culture dishes in which microdrops of medium are arranged with each dish containing approximately 100 $\mu$l drops (TL Hepes with Ca and Mg) containing the oocytes and 20 $\mu$l drops (TL Hepes with Ca and Mg and 20–50% fetal calf serum) to one side containing the cultured embryonic cells. The addition of between about 1 and 25% fetal calf serum, or other sera with activity similar to fetal calf serum, to the medium is beneficial in reducing the attraction, i.e., the adhesiveness, of the embryonic cells, thereby preventing cell agglutination and allowing easier handling during micromanipulation.

the micromanipulation process involves a cell holding pipette having an outer diameter of approximately 90–180 $\mu$m and an inner diameter of approximately 25–35 $\mu$m, and a beveled, sharpened enucleation micropipette having an outer diameter of approximately 10 to 45 $\mu$m, depending upon the size of the embryonic cell. The parthenogenically-activated oocyte is positioned on the holding pipette so that the polar body is towards the transfer tip. The polar body and a small amount of cytoplasm from the region directly beneath the polar body is removed.

The cells were then enucleated according to the procedures described in *Prather et al*. Preferably, enucleation can be verified by methods known in the art such as by staining with Hoechst 33342, a DNA stain, removing excess dye and visualization with ultra-violet (UV) light (excitation emission). Reference is made to Experiment 8 (infra.) for a more detailed description of this and the following procedures. Oocytes with no evidence of metaphase plate (enucleated oocyte) were selected.

The enucleated oocytes are then parthenogenically activated according to procedures described above. An example of a preferred activation procedure is described in Experiment 8, in which the oocytes are exposed to 5 $\mu$M ionomycin in TL-HEPES for approximately 4 minutes. The enucleated oocytes are then diluted in TL-HEPES (30 mg/ml bovine serum albumin [BSA]), are then diluted in TL-HEPES (1 mg/ml BSA). The oocytes are then placed in an activation medium CR1 containing 1.9 mM DMAP for approximately 3.5–5 hours. Following the DMAP step, the enucleated oocytes are again diluted in TL-HEPES (1 mg/ml BSA) and a blastomere, e.g., a donated nucleus, was inserted next to the oocyte. A slit is made in the *zona pellucida* of the oocyte and the embryonic cell is inserted therein. The cell is pressed against the cytoplasm where it sticks firmly to the cytoplasmic membrane. Due to the adhesion of the cells, transfer pipettes are changed frequently.

Cell Fusion

A variety of fusion techniques may be employed for this invention. For example, the onset of the electricity by electrofusion can induce the fusion process. Electrofusion is accomplished by providing a pulse of electricity that is sufficient to cause a transient breakdown of the plasma membrane. This breakdown of the plasma membrane is very short and the membrane reforms very rapidly. If two adjacent membranes are induced to breakdown and upon reformation the lipid bilayers intermingle, small channels will open between the two cells. Due to the thermodynamic instability of such a small opening, it enlarges until the two cells become one. Reference is made to Prather et al., which is incorporated herein by reference, for a further discussion of this process. A variety of electrofusion media can be used including sucrose, mannitol, sorbitol and phosphate buffer solution.

Fusion can also be accomplished using Sendai virus as a fusigenic agent (Graham, 1969).

Polyethylene glycol (PEG) may also be used as a fusigenic agent. Under prescribed conditions, PEG provides excellent fusion results. In one protocol, the cells are fused in PEG (molecular weight 1,300–1,600 Sigma), which is mixed in a solution containing TL Hepes (approximately 1:0.25 μg/ml) and polyvinyl alcohol (PVA) approximately 1 μg/ml), $Ca^{2+}$ and $Mg^{2+}$-free. The media containing the cells is then passed through one or more dilutions (approximately 1:1) of the above-described PEG media. The cell media is then allowed to rest in a culture media, such as TL Hepes containing fetal calf serum until the cell membranes return to a normal appearance. Experimental conditions will vary depending upon the products used.

The following experiments are illustrative of the present invention and are not intended to limit the invention in any way.

EXPERIMENTS

The following procedures are common to one or more of the experiments.

Oocyte Maturation

The chemicals used in the oocyte maturation process were purchased from Sigma Chemical Co., St. Louis, Mo., unless otherwise indicated. Preparations and concentrations of bovine serum albumin (BSA) are indicated for each media.

Bovine oocytes were obtained at an abattoir and transported to the laboratory in saline (30–34° C., transport time 2–6 hr). Oocytes from small follicles (1–6 mm) were aspirated and matured according to the methods described in Sirard et al., 1988. Briefly, oocytes were diluted out of the follicular fluid with 3 dilutions of TL HEPES modified by removing glucose, adding 0.22 mM pyruvate and 1 mg/ml of BSA (Fraction V, Sigma Chemical CO, St. Louis, Mo.).

The oocytes were placed in 50 μl drops of TCM-199 (Earle's Salts; Gibco, Grand Island, N.Y.) supplemented with 10% heat treated fetal calf serum, 0.22 mM pyruvate, 5 μg/ml FSH-P (Scherring-Plough Animal Health Corp., Kenilworth, N.J.) and 1 μ/ml estradiol. Ten oocytes were incubated in a 50 μl drop under paraffin oil for 24 hours at 39° C. in 5% $CO_2$ in air humidified atmosphere.

Activation

The cumulus was removed from matured oocytes by vortexing vigorously in 200 μl or TL-HEPES for 3 min. The denuded oocytes were diluted in 3 changes of TL-HEPES to separate the oocytes from the cumulus cells. Where indicated, the oocytes were exposed to 5 μM ionomycin (5 mM stock in DMSO; Calbiochem, La Jolla, Calif.) in TL-HEPES (1 mg/ml fatty acid free BSA) for 4 min. The oocytes were then diluted into TL-HEPES (30 mg/ml fatty acid BSA) for 5 min followed by dilution into TL-HEPES (1 mg/ml Fraction V BSA). The oocytes were then moved to 50 μl drops of embryonic cell development media (U.S. Pat. No. 5,096,822 to Rosenkrans et al., with or without DMAP (1.9 mM) for the indicated times (39° C., 5% $CO_2$ in air). Embryonic cell development media contained 114.6 mM NaCl, 3.1 mM KCl, 5 mM hemi-calcium lactate, 0.4 mM Na pyruvate, 1 mM glutamine, 3 mg/ml fatty acid free BSA, MEM nonessential amino acids and BME amino acids.

Activation and Development Assessment

Activation was evaluated at times indicated in each experiment. The oocytes were mounted on slides, fixed with acetic acid:alcohol (1:3) and observed with Nomarski optics. Special care was taken in determining if metaphase plates were metaphase II or aberrant metaphase III (Kubiak, 1989). Oocytes that contained a metaphase I or II plate were considered not activated. Oocytes that contained anaphase, telophase or metaphase II plates or pronuclei were considered to be activated.

In experiments that determined development potential of the parthenotes, activated oocytes were cultured for 7–8 days in embryonic cell development media. On the date after activation, initial cleavage was determined by visual observation. On day 4 of incubation 5% heat treated fetal calf serum was added to each drop. For some experiments, blastocysts were mounted and fixed in acetic acid:alcohol (1:3) and stained with 1% orcein dissolved in 40% acetic acid to determine cell numbers.

Data Analysis

Activation and development data were analyzed with the Statistical Analysis System statistical package (General Linear Models (Cary, N.C.). Means were tested by Duncan's Multiple Range Test.

Experiment 1

Effect of Sequential Exposure of Oocytes to Ionomycin and DMAP

Experiment 1 determined the effect of sequential exposure of oocytes to ionomycin and DMAP. One level of ionomycin (5 μM) and DMAP (1.9 mM) was used throughout all studies. The oocytes were cultured for 5 hours after ionomycin incubation with or without DMAP. Control oocytes were cultured in embryonic cell development medium alone. Activation was determined after 5 hours of culture.

Figure 1B:
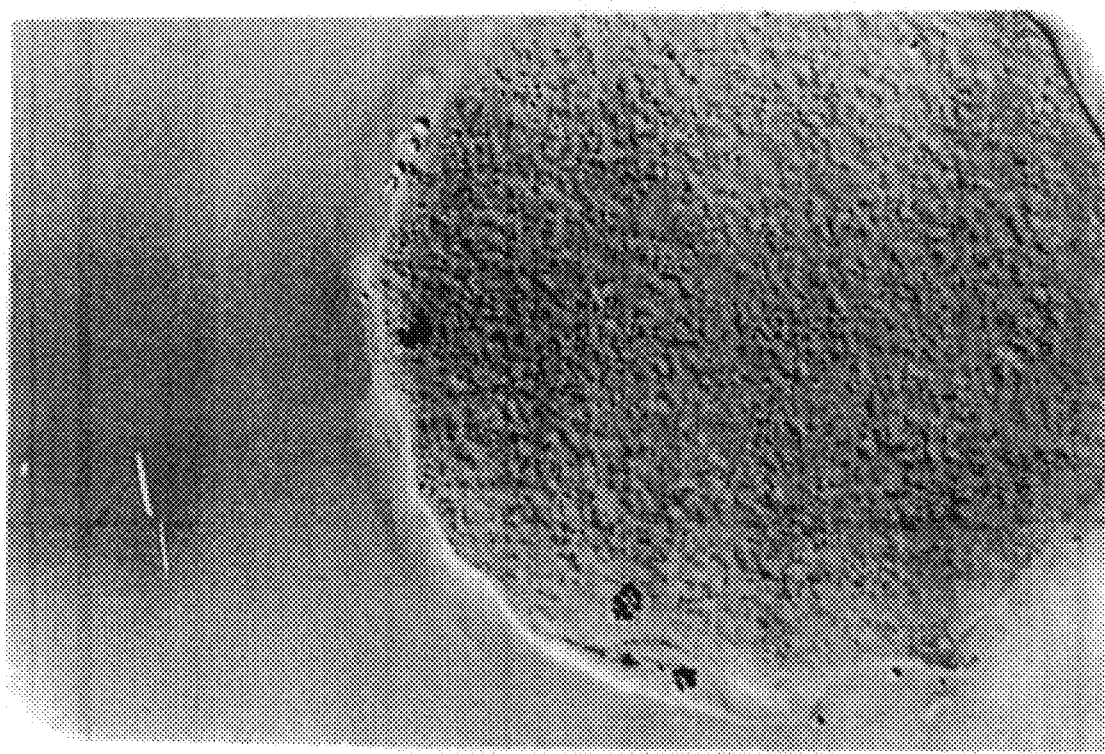
FIG. 1*b* is a photograph illustrating the activation of oocytes by ionomycin in Experiment 1.
Figure 1C:
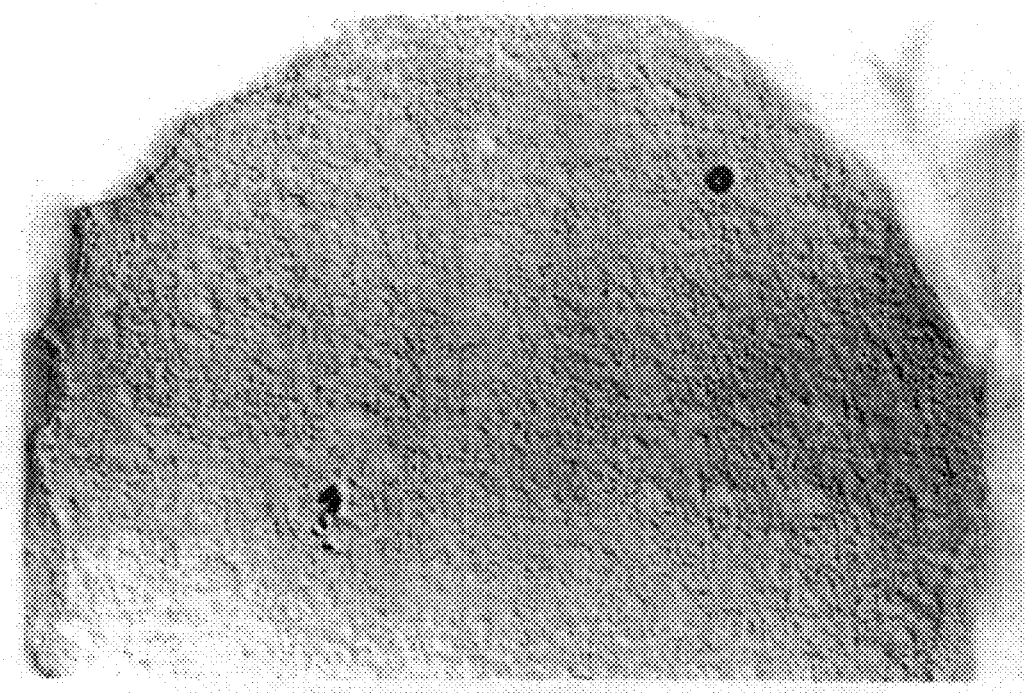
FIG. 1*c* is a photograph illustrating the activation of oocytes by DMAP alone in Experiment 1.

Reference is made to Table 1 following, which illustrates the effect of culture in ionomycin and DMAP for 5 hours on parthenogenic activation of the bovine oocytes matured for 24 hours, and to FIGS. 1a, 1b, and 1c to illustrate the results of Experiment 1.

TABLE 1

The effect of culture in Ionomycin and DMAP for 5 hours on parthenogenic activation of the bovine oocytes matured for 24 hours.[1]

| Treatment | N | % Activation | % Pronuclear formation |
|---|---|---|---|
| Control | 83 | 1.4 ± 1.4[a] | 0[a] |
| Ionomycin (5 μM) | 80 | 57.8 ± 7.8[b] | 8.9 ± 7.3[a] |
| DMAP (2 mM) | 93 | 7.8 ± 5.5[a] | 7.8 ± 5.5[a] |
| Ionomycin + DMAP | 91 | 80.5 ± 13.1[b] | 80.5 ± 13.1[b] |

[1]Letters within a column with different letters were different as tested with Duncan's Multiple Range Test (p < 0.05).

Figure 1D:
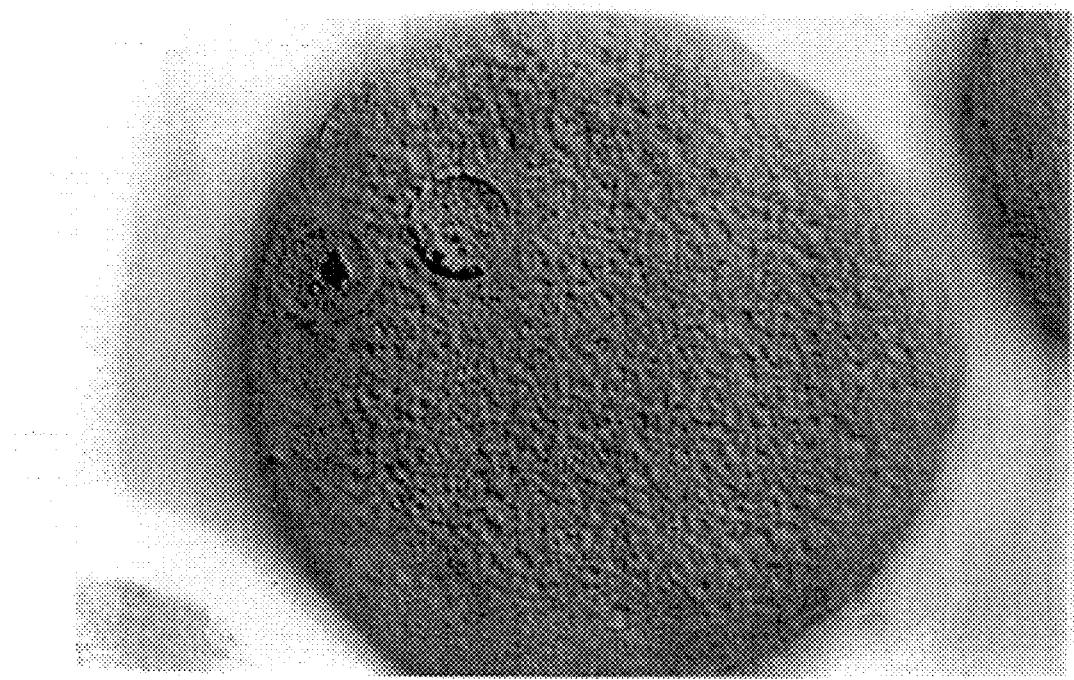
FIG. 1*d* is a photograph illustrating the activation of oocytes following sequential treatment of ionomycin and DMAP in Experiment 1.

A metaphase II bovine oocyte from the control treatment is shown in FIG. 1a. Ionomycin alone activated the oocytes to a high level but instead of forming pronuclei the chromosomes reassembled into a metaphase plate as illustrated in FIG. 1b. As illustrated in FIG. 1c, DMAP alone did not activate the oocytes but caused the chromosomes to form a tight clump in the cytoplasm. The sequential treatment of ionomycin and DMAP activated the oocytes more than either treatment alone and pronuclear formation was significantly higher than for the other treatments. It is interesting to note that these oocytes contain only 1 polar body, illustrated in FIG. 1d.

Experiments 2a and 2b

Effect of Time of Incubation in DMAP on Activation and Development

Experiments 2a and 2b determined the effect of time of incubation in DMAP on activation and development. In Experiment 2a, oocytes were incubated in DMAP for 15, 30, 60, 150 and 300 minutes. At the end of the incubation time indicated, oocytes were rinsed in TL-HEPES (1 mg/ml Fraction V BSA) and placed into embryonic cell development medium until 5 hours had elapsed. At 5 hours, a subsample of oocytes was removed and mounted to determine activation. The remaining oocytes were returned to the incubator for 7–8 days. Blastocytes on day 7–8 were rated as good or poor and cell number was determined.

Experiment 2b was similar in design except that oocytes were incubated for 2 hours, 3 hours, 4 hours, or 5 hours in DMAP.

The results of Experiment 2a are shown in the following Table 2, which illustrates the effect of time of incubation in DMAP on activation, pronuclear formation, initial cleavage and parthenogenic development:

TABLE 2

The effect of time of incubation of DMAP on activation, pronuclear formation, initial cleavage and parthenogenic development (r = 4)[1]

| Length of 6-DMAP Incubation (min) | N | Activation ($\pm$ se) | Pronuclear Formation ($\pm$ se) | N | Cleavage ($\pm$ se) | Development to Blastocyst ($\pm$ se)[2] |
|---|---|---|---|---|---|---|
| 0 | 76 | $58.2^{a,b}$ (4.6) | $1.4^a$ (1.4) | 95 | $3.4^a$ (3.4) | $0^a$ |
| 15 | 70 | $52.4^{a,b}$ (11.0) | $1.4^a$ (1.4) | 88 | $7.2^a$ (3.2) | $0^a$ |
| 30 | 80 | $37.8^{b,c}$ (11.4) | $2.5^a$ (2.5) | 103 | $4.4^a$ (2.1) | $0^a$ |
| 60 | 69 | $22.6^{b,c}$ (4.8) | $5.4^a$ (5.2) | 111 | $2.3^a$ (1.5) | $0.7^a$ $(0.7)^3$ |
| 150 | 79 | $32.9^{b,c}$ (6.3) | $31.6^b$ (6.5) | 105 | $30.9^b$ (10.4) | $9.9^b$ $(4.3)^4$ |
| 300 | 71 | $76.6^a$ (9.8) | $76.6^c$ (9.8) | 100 | $65.6^c$ (3.2) | $21.1^c$ $(1.5)^5$ |

[1]Percents within a column with different superscripts are different (P < 0.05).
[2]After day 7–8 of culture.
[3]Cell numbers for the blastocysts were good-83 (n = 1).
[4]Cell numbers for the blastocysts were good-70.8 $\pm$ 7.7 (n = 4); poor-25 (n = 1).
[5]Cell numbers for the blastocysts were good-61.7 $\pm$ 4.7 (n = 6); poor-22 $\pm$ 13.0 (n = 10).

Activation by ionomycin was not different from incubation in DMAP for 15 minutes. However, incubation in DMAP for 30–150 minutes resulted in a lowered activation. It appears that the DMAP is actively inhibiting activation. Exposure to DMAP for 150 minutes allows all the oocytes that are activated to progress to the pronuclear stage. At 300 minutes, there is a high level of activation and pronuclear formation. Cleavage and development are very low until the oocytes have been exposed to DMAP for 150 minutes and the rates are significantly higher at 300 minutes.

The results of Experiment 2b are shown in the following Table 3, which illustrates the effect of time of incubation in DMAP on activation, pronuclear formation, initial cleavage and parthenogenic development:

TABLE 3

The effect of time of incubation of DMAP on activation, pronuclear formation, initial cleavage and parthenogenic development (r = 3)[1]

| Length of DMAP Incubation (h) | N | Activation ($\pm$ se) | Pronuclear Formation ($\pm$ se) | N | Cleavage ($\pm$ se) | Development to Blastocyst ($\pm$ se)[2] |
|---|---|---|---|---|---|---|
| 0 | 70 | $67.1^a$ (8.4) | $7.1^a$ (3.2) | 84 | $19.2^a$ (3.0) | $0^a$ |
| 2 | 72 | $39.9^b$ (11.2) | $34.9^b$ (6.3) | 97 | $21.6^a$ (1.2) | $3.3^a$ (3.3) |
| 3 | 72 | $75.8^{bc}$ (5.9) | $75.8^c$ (5.9) | 103 | $66.5^b$ (5.2) | $33.3^b$ (5.1) |
| 4 | 70 | $75.8^{bc}$ (7.8) | $75.8^c$ (7.8) | 96 | $63.5^a$ (3.8) | $26.5^b$ (5.2) |
| 5 | 71 | $86.3^c$ (1.6) | $86.3^c$ (1.6) | 98 | $70.4^b$ (9.1) | $28.9^b$ (3.6) |

[1]Percents within a column with different superscripts are different (P < 0.05).
[2]Day 7–8 of culture.

As seen in the Experiment 2, activation was significantly lower at 2 hours of DMAP incubation than ionomycin alone or 3 hours, 4 hours or 5 hours of DMAP incubation. Pronuclear formation of oocytes treated with ionomycin alone was significantly lower than any incubation in DMAP. Incubation in DMAP for 3 hours, 4 hours or 5 hours was not different. Initial cleavage of ionomycin alone or ionomycin+ DMAP 2 hours was not different and was significantly lower than 3 hours, 4 hours or 5 hours of DMAP incubation. Blastocyst development was not significantly different at 3 hours, 4 hours or 5 hours of DMAP incubation.

Reference is also made to Table 4, which illustrates the effect of time of incubation in DMAP on the cell number in resulting parthenote blastocysts:

TABLE 4

The effect of time of incubation in DMAP on the cell number in resulting parthenote blastocysts (r = 3).

| Length of DMAP Incubation (h) | N | Good | ($\pm$ se) | N | Poor | ($\pm$ se) |
|---|---|---|---|---|---|---|
| 2 | 3 | 88.7 | (6.3) | 0 | | |
| 3 | 19 | 70.1 | (6.6) | 7 | 33.1 | (4.9) |
| 4 | 11 | 73.6 | (7.2) | 7 | 40.1 | (11.4) |
| 5 | 15 | 83.7 | (10.0) | 4 | 44 | (9.3) |

Cell numbers of the blastocyst generated were not different within quality classification.

Experiment 3

Kinetics of Activation When Oocytes Were Exposed to Ionomycin Alone or to Ionomycin Followed by a 3 Hour Incubation in DMAP Experiment 3 was designed to determine the kinetics of activation when oocytes were exposed to ionomycin alone or to ionomycin followed by a 3 hour incubation in DMAP. At the end of the 3 hour incubation, oocytes in DMAP were diluted in TL-HEPES (1 mg/ml Fraction V BSA) and moved to embryonic cell development medium until mounting. A sample of oocytes from both treatments were mounted at 1, 2, 3, 4 and 5 hours after exposure to ionomycin to determine the activation state.

Figure 2:
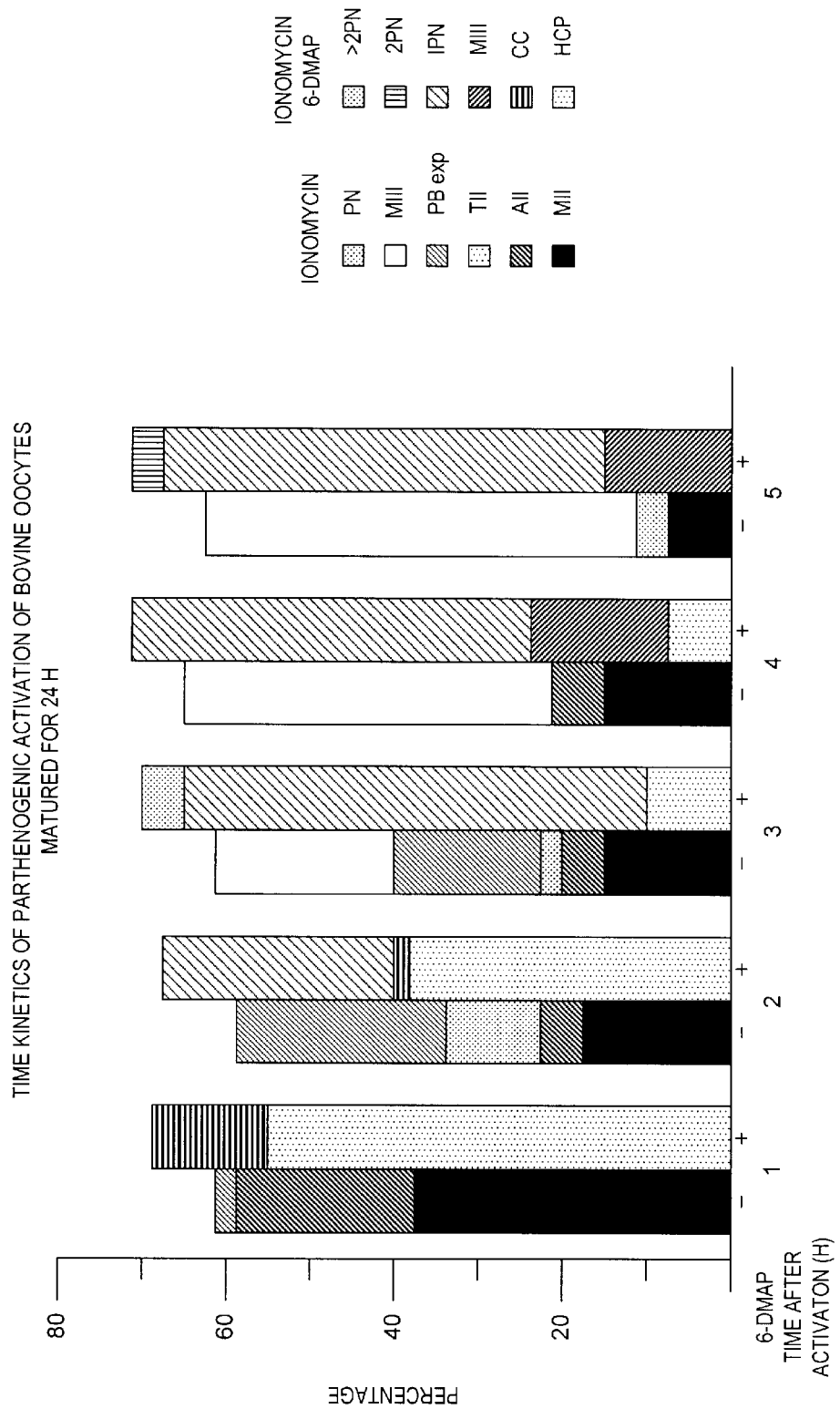
FIG. 2 illustrates the kinetics of parthenogenic activation of the bovine oocyte (matured for 24 h) by ionomycin or ionomycin and 6-DMAP. Oocytes were treated and samples mounted and fixed for evaluation after 1, 2, 3, 4, or 5 h incubation. The nuclear stage was determined by observation with Normarski optics.

The results of Experiment 3 are illustrated in FIG. 2, which is a graph illustrating the kinetics of parthenogenic activation of the bovine oocyte (matured for 24 hours) by ionomycin and 6-DMAP. When the oocytes were treated with ionomycin alone, they had resumed meiosis by 1 hour and there was evidence of polar body expulsion by 2 hours. By 4–5 hours, the oocytes were arrested in metaphase III. In contrast, when the oocytes were exposed to the sequential treatment of ionomycin+DMAP, there was evidence of pronuclear formation by 2 hours and maximum pronuclear formation by 3 hours. There was no evidence of arrest in metaphase III. These data imply that DMAP works by inhibiting resumption of meiosis and forces the cells to enter mitosis without the second reduction division.

Experiment 4

Time at which DMAP is Necessary for Parthenogenic Activation Relative to the Exposure to Ionomycin Experiment 4 was designed to determine the time at which DMAP is necessary for parthenogenic activation relative to the exposure to ionomycin. The oocytes were exposed to ionomycin and placed in embryonic cell development medium. At 0, 1, 2, 2.5, 3 and 4 hours after ionomycin exposure, oocytes were placed in embryonic cell development medium+DMAP. At 5 hours post ionomycin exposure, the oocytes were mounted to determine their activation state.

Figure 3:
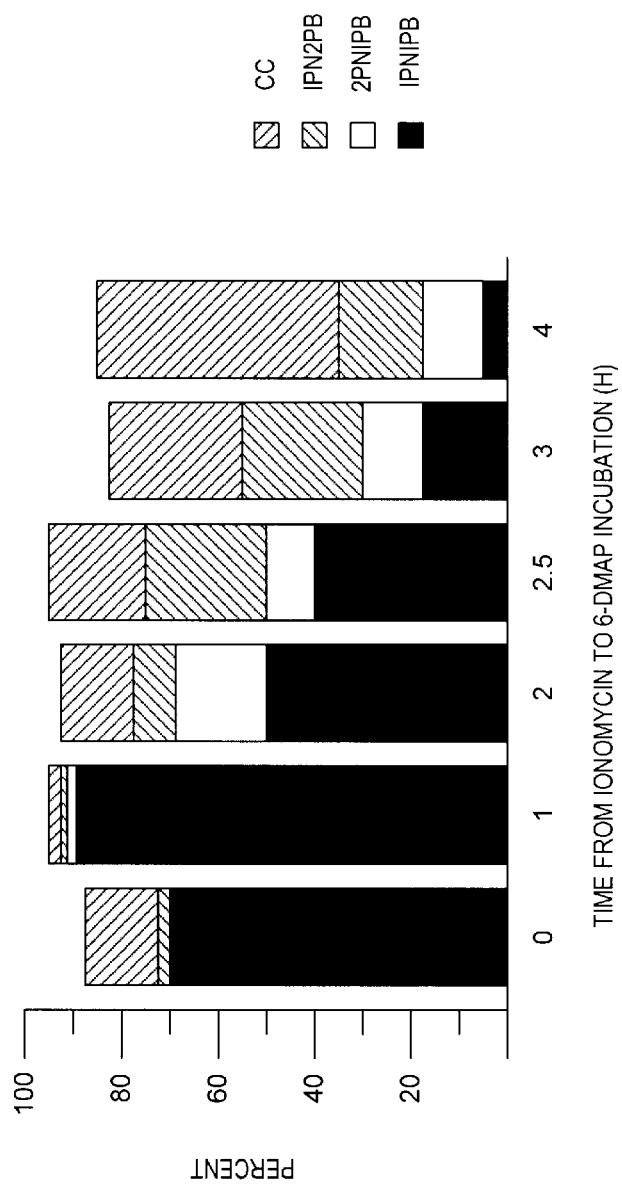
FIG. 3 illustrates the effect of time from ionomycin treatment to 6-DMAP treatment on the parthenogenic activation of 24 h bovine oocytes (r=3). Oocytes were mounted after a total of 5 h incubation and accessed for DNA form. Activated oocytes which rated as having clumped chromatin (CC), one pronucleus and two polar bodies (1PN2PB), two pronuclei and one polar body (2PN1PB), or one pronucleus and one polar body (1PN1PB).

The results of Experiment 4 are illustrated in FIG. 3, which shows the effect of time from ionomycin treatment to 6-DMAP treatment on the parthenogenic activation of 24-hour bovine oocytes. As the interval from ionomycin treatment to exposure to DMAP increased to more than 1 hour, the oocytes showed an increase in ability to resume meiosis to form either a second pronucleus or a single pronucleus and 2 polar bodies. Experiment 3 showed that at 2 hours, oocytes treated with ionomycin alone had resumed meiosis and ranged from anaphase to polar body expulsion. These data imply that DMAP may force the chromatin to be converted to pronuclei or clumped chromatin.

Experiment 5

Initiating and Sustaining Pregnancy with Parthenote Blastocysts

Experiment 5 was designed to determine if parthenote blastocysts could initiate and sustain a pregnancy. Blastocysts were generated by treatment with ionomycin followed by a 3 hour incubation in 6-DMAP. After 7 days in culture, blastocysts that were rated as good or excellent were non-surgically transferred to the uterus of Holstein heifers that were in heat 6–7 days prior to transfer. Two blastocysts were transferred per recipient, 1 contralateral and 1 ipsilateral to the ovary that had been palpated to contain the corpus luteum (CL). Cows were checked for signs of estrus twice daily and Kamar® Heatmount Detectors were used to aid in heat detection (Kamar, Inc.; Steamboat Springs, Colo.). Recipients were palpated every 3–4 days after day 21–23 of the cycle. Ultrasound was used to detect uterine vesicles and to assess CL presence.

The results of Experiment 5 are illustrated in the following Table 5, which illustrates embryonic cell transfer of blastocysts resulting from parthenogenic activation of bovine oocytes with ionomycin and DMAP.

TABLE 5

Embryonic cell transfer of blastocysts resulting from parthenogenic activation of bovine oocytes with ionomycin and DMAP

| | |
|---|---|
| Total transfers (n) | 22 |
| Extended cycle (%)[a] | 7 (32.0%) |
| Intra estrual interval (d) | |
| Normal | 20.9 ± 0.5 |
| Extended | 29.8 ± 2.2 |

[a]Cycles > 24 days.

Table 5 shows that parthenote blastocysts establish prolonged estrous cycles in bovine. Relatively fewer transfers resulted in prolonged estrous cycles, CLs and uterine vesicles (32%), than in the mouse (Graham, 1974; Tarkowski, 1975 (62%); Siracusa et al., 1978). The extended cycles had a mean of 29.8±2.2 days.

Experiment 6

Use of Parthenogenically Activated Aged Oocytes in a Nuclear Transfer Procedure Bovine oocytes were obtained and placed in maturation media for approximately 20 hours. The cumulus cells were then stripped off the oocytes according to the previously described procedures.

The oocytes were then enucleated according to Prather et al. and placed in CR1aa maturation medium until 40 hours had elapsed. The oocyte were then placed in CR1aa maturation medium with 1.9 mM DMAP for 2 hours and incubated at room temperature activation (RTC) conditions (about 25° C.).

Following incubation, embryonic cells were transferred into the oocytes and the 2 cells were electrically fused together according to the procedures described in Prather et al., with the exception of the step of waiting until 42 hours to activate via RTC (25° C.) and adding DMAP prior to the time of electrofusion. The fused nuclear transfer embryos were then cultured in maturation medium CR1aa for 6 to 7 days to determine developmental rates to the blastocyst stage.

Reference is made to table 6 for results of this experiment:

TABLE 6

Development of 42-hour oocyte derived nuclear transfer (NT) embryos

| Treatment | # NTs to Culture | Number Blastocyst | Number Usable Blastocyst |
|---|---|---|---|
| RTC (2 hours) | 146 | 29 (20%) | 11 (8%) |
| DMAP & RTC (2 hours) | 140 | 40 (29%) | 18 (13%) |

Table 6 shows that DMAP can be used in the nuclear transfer procedure along with other activation stimuli such as room temperature activation (RTC) to increase developmental rates to the blastocyst stage in aged oocytes (42 hour oocytes). RTC has been shown to be similar to an electrical pulse or ionomycin activation stimulus (Stice and Keefer, 1992).

Experiment 7

Use of Parthenogenically Activated Young Oocytes in a Nuclear Transfer Procedure This experiment was conducted under similar conditions as Experiment 6 with the exception that the oocytes were either placed directly in DMAP (young oocytes) or given in ionomycin (5 $\mu$M) treatment for 4 minutes plus DMAP treatment immediately after enucleation, i.e., at 20 hours maturation. At the end of the DMAP treatment, approximately 24 hours, embryonic cells were transferred into the oocytes and electrofusion was induced. The concentration of activating chemicals used were the same as those described in Experiment 6. The embryos were placed in maturation medium CR1aa for 6 to 7 days to determine developmental rates to blastocyst stage. The results of this experiment are found in the following Table 7:

TABLE 7

Development of 20-hours oocytes derived nuclear transfers (fused after activation)

| Treatment | Number Oocytes | Cleavage Rate | Development Rate to Blastocyst | % Usable |
|---|---|---|---|---|
| 4 Hours DMAP (Serum) | 60 | 4% | 0% | 0% |
| Ionomycin & 4 hours DMAP (BSA & Serum)[1] | 273 | 65% | 24% | 18% |

[1]Activation Rate For Control Oocytes (BSA & Serum) 77/177 (44%)

Experiment 8

Use of 24-hour Parthenogenically Activated Oocytes for Nuclear Transfer

Cumulus cells were removed from bovine oocytes at 21–22 hours maturation by vortexing the oocytes in 200 $\mu$l TL-HEPES for approximately 3 minutes. The cells were then enucleated according to the procedures described in Prather et al. Enucleation was verified by staining with 10 mg/ml Hoechst 33342, a DNA stain, for approximately 20 minutes, removing excess dye and visualization with ultraviolet (UV) light (excitation emission). Oocytes with no evidence of metaphase plate (enucleated oocyte) were selected.

The enucleated oocytes were exposed to 5 $\mu$M ionomycin in TL-HEPES for approximately 4 minutes. The enucleated oocytes were then diluted in TL-HEPES (30 mg/ml bovine serum albumin [BSA]), and then diluted in TL-HEPES (1 mg/ml BSA).

The oocytes were then placed into maturation medium CR1 containing 1.9 mM DMAP for approximately 3.5–5 hours. Following the DMAP step, the enucleated oocytes were diluted in TL-HEPES (1 mg/ml BSA) and a blastomere, e.g., a donated nucleus, was inserted next to the oocyte.

The blastomere was electrofused to the enucleated oocyte according to procedures described in Prather et al. at 100° V for about 30 $\mu$secs. in a 1 mm chamber. The electrofused nuclear transfer was incubated in maturation medium CR1aa (1 mg/ml BSA) for 6 to 7 days. On day 4, 5% heat-treated fetal calf serum was added.

The results are shown on the following Table 8:

TABLE 8

Use of 24-hour oocytes for nuclear transfer using activation by Ionomycin (5 $\mu$M) + 6-DMAP (1.9 mM)

| | Ionomycin + DMAP | | | Control[1] | | |
|---|---|---|---|---|---|---|
| | R[2] | n[3] | % ± SE | R | n | % ± SE |
| Enucleation | 11 | 68 | 91.2 ± 3.0 | | | |
| Fusion | 11 | 443 | 91.8 ± 1.5 | 8 | 141 | 90.3 ± 2.2 |
| ≧2 Cell (d 2) | 12 | 428 | 86.0 ± 2.0 | 8 | 127 | 46.1 ± 6.9 |
| BL (d 6–7) | 11 | 384 | 31.5 ± 3.7 | 7 | 109 | 5.7 ± 1.6 |

[1]Nuclear transfer units not exposed to ionomycin or DMAP but fused at similar oocyte age as the treated oocytes.
[2]R = No replicates performed
[3]N = Number of units evaluted Following incubation in DMAP, the oocytes are diluted in TL-HEPES (1 mg/ml BSA) and incubated in CR1aa (1 mg/ml BSA).

It is understood that the invention is not confined to the particular construction and arrangement herein described, but embraces such modified forms thereof as come within the scope of the following claims.

REFERENCES

Collas, P. and J. M. Robl. 1990. "Factors affecting the efficiency of nuclear transplantation in the rabbit embryo." *Biol. Reprod.* 43:877–884.

Cuthbertson, K. S. R. 1983. "Parthenogenic activation of mouse oocytes in vitro with ethanol and benzyl alcohol." *J. Exp. Zool.* 226:311–314.

First, N. L., Leibfried-Rutledge, M. L., Northey, D. L. and Nuttleman, P. R. 1992. "Use of in vitro matured oocytes 24 h of age in bovine nuclear transfer." *Theriogenology* 37:211.

First, N. L. and R. Prather. 1991. "Genomic Potential in Mammals," *Differentiation*, 48:1–8.

Fissore, R. A. and J. M. Robl. 1992. "Intracellular $Ca^{2+}$ response of rabbit oocytes to electrical stimulation." *Mol. Reprod. Dev.* 32:9–16.

Graham, C. F. 1969. "The fusion of cells with one and two cell mouse embryos," *Wistar Inot. Symp. Monogr.,* 9:19.

Graham, C. F. 1970. "Parthenogic mouse blastocysts." *Nature* 242:475–476.

Graham, C. F. 1974. "The production of parthenogenic mammalian embryos and their use in biological research." *Biol. Rev.* 49:399–422.

Gray, K. R., K. R. Bondioli and C. L. Betts. 1991. "The commercial application of embryo splitting in beef cattle." *Theriogenology* 35:37–45.

Kaufman, M. H. 1981. "Parthenogenesis: a system facilitating understanding of factors that influence early mammalian development. *Prog. in Anat.*, Vol. 1, 1–34.

Kline, D. and Kline, J. T. 1992. "Repetitive calcium transients and the role of calcium in exocytosis and cell cycle activation in the mouse egg." *Dev. Biol.* 149:80–89.

Masui, Y. and Markert, C. L. 1971. "Cytoplasmic control of nuclear behavior during meiotic maturation of frog oocytes." *J. Exp. Zool.* 177, 129–146.

Nagai, T. 1987. "Parthenogenic activation of cattle follicular oocytes in vitro with ethanol." *Gamete Res.* 16:243–249.

Nurse, P. 1990. "Universal control mechanism regulating onset of M-phase." *Nature* 344:503–508.

Onodera, M. and Y. Tsunoda. 1989. "Parthenogenetic activation of mouse and rabbit eggs by electric stimulation in vitro." *Gamete Research* 22:277–283.

Ozil, J. P. 1990. "The parthenogenetic development of rabbit oocytes after repetitive pulsatile electrical stimulation." *Development* 109:117–127.

Prather et al., U.S. Pat. No. 4,994,384

Rickord, L. F. and White, K. L. 1992. "Electrofusion-induced intracellular $Ca^{+2}$ flux and its effect on murine oocyte activation." *Mol. Reprod. Dev.* 31:152–159.

Rosenkrans, U.S. Pat. No. 5,096,822.

Siracusa, G., Whittingham, D. G., Molinaro, M. and Vivarelli, E. 1978. "Parthenogenic activation of mouse oocytes induced by inhibitors of protein synthesis." *J. Embryol. exp. Morph.* 43:157–166.

Sirard, M. A., J. J. Parrish, C. B. Ware, M. L. Leibried-Rutledge and N. L. First. 1988. "The culture of bovine oocytes to obtain developmentally competent embryos." *Biol. Reprod.* 39:546–552.

Steinhardt, R. A., Epel, D. and Yanagimachi, R. 1974. "Is calcium ionophore a universal activator for unfertilized eggs?" *Nature* 252:41–43.

Stice, S. L. and Robl, J. M. 1990. "Activation of mammalian oocytes by a factor obtained from rabbit sperm." *Mol. Reprod. Dev.* 25:272–280.

Stice, S. L. and Keefer, C. 1992. "Improved development rates for bovine nucleus transfer embryos using cold shock activated oocytes." *Biol. Reprod.* 42 (Suppl 1):166.

Surani, M. A. H. and Kaufmann, N. H. 1977. "Influence of extracellular $Ca^{2+}$ and $Mg^{2+}$ ions on the second meiotic division of mouse oocytes: Relevance to obtaining haploid and diploid parthenogenetic embryos." *Dev. Biol.* 59:86–90.

Susko-Parrish, J. L., Nuttleman, P. R. and Leibfried-Rutledge, M. L. 1991. "Effect of bovine oocyte aging in vitro on development." *Biol. Reprod.* 44(Suppl 1):17:156 (abstract).

Swann, K. 1990. "A cytosolic sperm factor stimulates repetitive calcium increases and mimics fertilization in hamster eggs." *Development* 110:1295–1302.

Tarkowski, A. K., Witkowska, A. and Nowicka, J. 1970. "Experimental parthenogenesis in the mouse." *Nature* 226:162–165.

Tarkowski, A. K. 1975. "Recent studies on parthenogenesis in the mouse." In: *The Developmental Biology of Reproduction* (C. L. Markert, E. J. Papaconstantinon, eds.), pp. 107–129, New York: Academic Press.

Tombes, R. M., Simerly, C., Borisy, G. G. and Schatten, G. 1992. "Meiosis, egg activation and nuclear envelope breakdown are differentially reliant on $Ca^{+2}$, whereas germinal vesicle breakdown is $Ca^{+2}$ independent in the mouse oocyte." *J. Cell Biol.* 117:799–811.

Ware, C. B., Barnes, F. L., Maiki-Laurila, M. and First, N. L. 1989. "Age dependence of bovine oocyte activation." *Gamete Res.* 22:265–275.

Watanabe, N., Hunt, T. Ikawa, Y. and Sagata, N. 1989. "Specific proteolysis of the c-mos proto-oncogene product by calpain on fertilication of Xenopus eggs." *Nature* 342:505–510.

Watanabe, N., Hunt, T., Ikawa, Y. and Sagata, N. 1991. "Independent inactivation of MPF and cytostatic factor (mos) upon fertilization of Xenopus eggs." *Nature* 352:247–248.

Whitaker, M. and Patel, R. 1990. "Calcium and cell cycle control." *Development* 108:525–542.

Whitaker, M. and Irvine, F. R. 1984. "Inositol 1,4,5-trisphophate microinjection activates sea urchin eggs." *Nature* (London) 312:636–639.

Yang, X., Jiang, S. and Shi, Z. 1992. "Improved activation by combined cycloheximide and electric pulse treatment of bovine follicular oocytes matured in vitro for 23–24 hours." *Biol. Reprod.* 42(Suppl 1): 117.

Other embodiments are set forth within the following claims.

We claim:

1. A method of producing an activated mammalian oocyte, the method comprising:

activating a metaphase II-stage mammalian oocyte under conditions that prevent a nucleated metaphase II-stage mammalian oocyte from undergoing a second meiotic reduction division, whereby said activated mammalian oocyte is produced.

2. A method according to claim 1, wherein said conditions comprise:

increasing intracellular levels of divalent cations in said metaphase II-stage mammalian oocyte; and reducing phosphorylation of cellular proteins in said metaphase II-stage mammalian oocyte.

3. The method of claim 2, wherein intracellular levels of divalent cations are increased by introducing a divalent cation into the metaphase II-stage mammalian oocyte cytoplasm.

4. The method of claim 3 wherein the divalent cation is selected from the group consisting of magnesium, strontium, barium and calcium.

5. The method of claim 4 wherein the divalent cation is a free calcium ion.

6. The method of claim 3 wherein the divalent cation is introduced by an ionophore.

7. The method of claim 6 wherein the ionophore is selected from the group consisting of ionomycin and A23187.

8. The method of claim 2 wherein the intracellular levels of divalent cations are increased by electric shock.

9. The method of claim 2, wherein the intracellular levels of divalent cations are increased by treatment with ethanol.

10. The method of claim 2, wherein the intracellular levels of divalent cations are increased by treatment with caged chelators.

11. The method of claim 2 wherein phosphorylation of cellular proteins is reduced by inhibiting phosphorylation.

12. The method of claim 11 wherein the method of inhibiting phosphorylation comprises adding an effective phosphorylation inhibiting amount of a serine-threonine kinase inhibitor to the oocyte.

13. The method of claim 12, wherein the serine-threonine kinase inhibitor is selected from the group consisting of 6-dimethylaminopurine, staurosporine, 2-aminopurine, and sphingosine.

14. The method of claim 13 wherein the serine-threonine kinase inhibitor is 6-dimethylaminopurine.

15. The method of claim 2 wherein phosphorylation of cellular proteins is reduced by inducing dephosphorylation in the oocyte.

16. The method of claim 15 comprising introducing a dephosphorylizing amount of a phosphatase to the oocyte.

17. The method of claim 16 wherein the phosphatase is selected from the group consisting of Phosphatase 2A and Phosphatase 2B.

18. The method of claim 1, wherein said metaphase II-stage mammalian oocyte is a bovine oocyte.

19. The method of claim 1, wherein said metaphase II-stage mammalian oocyte is enucleated prior to said activating step.

20. The method of claim 1, wherein said metaphase II-stage mammalian oocyte is produced by maturing an immature mammalian oocyte in vitro.

21. A diploid parthenogenically activated mammalian oocyte comprising a single pronucleus.

22. The diploid parthenogenically activated mammalian oocyte comprising a single pronucleus of claim 21, wherein said mammalian oocyte is a bovine oocyte.

* * * * *